(12) United States Patent
Hebert

(10) Patent No.: US 6,237,359 B1
(45) Date of Patent: May 29, 2001

(54) UTILIZATION OF HARVEST AND/OR MELT WATER FROM AN ICE MACHINE FOR A REFRIGERANT SUBCOOL/PRECOOL SYSTEM AND METHOD THEREFOR

(76) Inventor: Thomas H. Hebert, 1340 Eastwood Dr., Lutz, FL (US) 33612

( * ) Notice: Subject to any disclaimer, the term of this patent is extended or adjusted under 35 U.S.C. 154(b) by 0 days.

(21) Appl. No.: 09/168,815

(22) Filed: Oct. 8, 1998

Related U.S. Application Data

(60) Provisional application No. 60/087,372, filed on May 28, 1998.

(51) Int. Cl.[7] .................................................. F25C 1/00
(52) U.S. Cl. ........................................ 62/348; 62/506
(58) Field of Search .............................. 62/348, 347, 352, 62/506

(56) References Cited

U.S. PATENT DOCUMENTS

| | | | |
|---|---|---|---|
| 1,891,538 | 12/1932 | Hicks | 62/526 |
| 2,124,291 | 7/1938 | Fleisher | 62/526 |
| 2,255,585 | 9/1941 | Hubacker | 62/526 |
| 2,350,408 | 6/1944 | McGrath | 62/510 |
| 2,351,695 | 6/1944 | Newton | 62/510 |
| 2,776,543 | 1/1957 | Ellenberger . | |
| 2,801,524 | 8/1957 | Fifield . | |
| 2,938,361 | 5/1960 | McNatt . | |
| 3,264,839 | 8/1966 | Harnish | 62/160 |
| 3,537,274 | 11/1970 | Tilney . | |
| 3,902,551 | 9/1975 | Lim et al. | 165/111 |
| 4,262,489 | * 4/1981 | Sakamoto | 62/348 |
| 4,320,629 | 3/1982 | Nakagawa et al. . | |
| 4,338,794 | * 7/1982 | Haais, Jr. | 62/348 |
| 4,375,753 | 3/1983 | Imasu et al. . | |
| 4,542,786 | 9/1985 | Anders | 165/144 |
| 4,574,868 | 3/1986 | Anders | 165/144 |
| 4,599,870 | 7/1986 | Hebert . | |
| 4,679,404 | 7/1987 | Alsenz | 62/175 |
| 4,873,837 | 10/1989 | Murray . | |
| 4,910,972 | 3/1990 | Jaster . | |
| 5,011,524 | * 4/1991 | Ruff | 62/348 |
| 5,205,347 | 4/1993 | Hughes | 165/1 |
| 5,275,232 | 1/1994 | Adkins et al. . | |
| 5,345,778 | 9/1994 | Roberts | 62/256 |
| 5,465,591 | 11/1995 | Cur et al. . | |
| 5,485,732 | 1/1996 | Locatelli . | |
| 5,613,554 | 3/1997 | Bull et al. | 165/150 |
| 6,000,228 | * 12/1999 | Johnson et al. | 62/348 |

FOREIGN PATENT DOCUMENTS

| | | |
|---|---|---|
| 559983 | 9/1983 | (EP) . |
| 2056652 | 3/1981 | (GB) . |

OTHER PUBLICATIONS

U.S. application No. 09/058,632, Hebert, filed Apr. 10, 1998.

* cited by examiner

Primary Examiner—William E. Tapolcai
(74) Attorney, Agent, or Firm—Holland & Knight LLP

(57) ABSTRACT

A system for providing liquid refrigerant subcooling, subsequent to that subcooling accomplished by the primary condenser of an ice machine, by means of utilizing cold harvest and/or melt water discharge from said ice machine. The subcooler is connected in fluid communication with the output of a pump that pumps stored ice machine discharge water to directly flow through the subcooler from a bottom portion to a top portion in a counter-flow direction and then to discharge such that the subcooler utilizes the pumped and flowing cold discharge water from the ice machine for providing maximum available subcooling to the liquid refrigerant of said ice machine

1 Claim, 13 Drawing Sheets

Valves A & B are solenoids.
A allows refrigerant flow through inlet water precooler when in ice making mode.
B bypasses refrigerant, past precooler when in harvest mode.
Same operation for Ice Bin Chiller.

Typical 24,000 Btuh* Compressor Performance Table

Refrigerant: R-22  
Motor: 2-Pole  
Subcooling: 15.0° F

Displacement: 2.44 in^3  
Voltage: 230-1-60  
Superheat: 20.0° F

| Condenser Temperature (°F) | | Evaporator Temperature (°F) | | | | | | | | | |
|---|---|---|---|---|---|---|---|---|---|---|---|
| | | 0 | 5 | 10 | 15 | 20 | 25 | 30 | 35 | 40 | 45 |
| 80 | Capacity (Btu/Hr) | 10748 | 12626 | 14680 | 16919 | 19351 | 21985 | 24830 | 27894 | 31186 | 34714 |
| | Power (watts) | 1216 | 1267 | 1313 | 1352 | 1384 | 1407 | 1420 | 1422 | 1413 | 1392 |
| | Current (Amps) | 5.4 | 5.6 | 5.8 | 6.0 | 6.1 | 6.3 | 6.3 | 6.4 | 6.4 | 6.3 |
| | Mass Flow (Lbs/Hr) | 135.4 | 157.0 | 180.1 | 204.7 | 230.9 | 258.9 | 288.7 | 320.4 | 354.1 | 389.8 |
| | EER (Btu/(W Hr)) | 8.84 | 9.96 | 11.18 | 12.51 | 13.98 | 15.63 | 17.49 | 19.61 | 22.07 | 24.94 |
| 90 | Capacity (Btu/Hr) | 9762 | 11552 | 13510 | 15645 | 17966 | 20482 | 23201 | 26132 | 29283 | 32664 |
| | Power (watts) | 1262 | 1326 | 1384 | 1436 | 1481 | 1518 | 1546 | 1564 | 1572 | 1567 |
| | Current (Amps) | 5.6 | 5.8 | 6.1 | 6.3 | 6.5 | 6.7 | 6.8 | 6.9 | 7.0 | 6.9 |
| | Mass Flow (Lbs/Hr) | 130.1 | 152.2 | 176.0 | 201.5 | 228.9 | 258.2 | 289.5 | 323.0 | 358.6 | 396.6 |
| | EER (Btu/(W Hr)) | 7.74 | 8.71 | 9.76 | 10.89 | 12.13 | 13.49 | 15.00 | 16.70 | 18.63 | 20.84 |
| 100 | Capacity (Btu/Hr) | 8773 | 10473 | 12334 | 14366 | 16576 | 18973 | 21566 | 24364 | 27375 | 30608 |
| | Power (watts) | 1302 | 1378 | 1449 | 1515 | 1574 | 1626 | 1669 | 1704 | 1728 | 1740 |
| | Current (Amps) | 5.7 | 6.1 | 6.4 | 6.7 | 6.9 | 7.2 | 7.4 | 7.5 | 7.6 | 7.6 |
| | Mass Flow (Lbs/Hr) | 120.8 | 142.8 | 166.7 | 192.6 | 220.6 | 250.7 | 283.0 | 317.7 | 354.8 | 394.4 |
| | EER (Btu/(W Hr)) | 6.74 | 7.60 | 8.51 | 9.48 | 10.53 | 11.67 | 12.92 | 14.30 | 15.85 | 17.59 |
| 110 | Capacity (Btu/Hr) | 7764 | 9376 | 11141 | 13068 | 15167 | 17445 | 19912 | 22576 | 25447 | 28531 |
| | Power (watts) | 1333 | 1421 | 1505 | 1585 | 1659 | 1726 | 1785 | 1836 | 1877 | 1908 |
| | Current (Amps) | 5.9 | 6.3 | 6.6 | 7.0 | 7.3 | 7.6 | 7.9 | 8.1 | 8.2 | 8.3 |
| | Mass Flow (Lbs/Hr) | 109.4 | 130.8 | 154.4 | 180.1 | 208.1 | 238.4 | 271.2 | 306.6 | 344.6 | 385.3 |
| | EER (Btu/(W Hr)) | 5.83 | 6.60 | 7.40 | 8.24 | 9.14 | 10.11 | 11.15 | 12.30 | 13.55 | 14.95 |
| 120 | Capacity (Btu/Hr) | 6724 | 8246 | 9914 | 11737 | 13724 | 15884 | 18225 | 20755 | 23484 | 26421 |
| | Power (watts) | 1350 | 1451 | 1549 | 1643 | 1732 | 1815 | 1891 | 1958 | 2017 | 2066 |
| | Current (Amps) | 5.9 | 6.4 | 6.8 | 7.3 | 7.6 | 8.0 | 8.3 | 8.6 | 8.8 | 9.0 |
| | Mass Flow (Lbs/Hr) | 98.1 | 118.4 | 141.0 | 166.0 | 193.5 | 223.6 | 256.3 | 291.8 | 330.1 | 371.3 |
| | EER (Btu/(W Hr)) | 4.98 | 5.68 | 6.40 | 7.14 | 7.92 | 8.75 | 9.64 | 10.60 | 11.64 | 12.79 |
| 130 | Capacity (Btu/Hr) | 5637 | 7069 | *8641* | 10360 | 12235 | 14276 | 16490 | 18887 | 21474 | 24262 |
| | Power (watts) | 1350 | 1465 | 1578 | 1686 | 1791 | 1890 | 1982 | 2067 | 2144 | 2212 |
| | Current (Amps) | 5.9 | 6.4 | 6.9 | 7.4 | 7.9 | 8.3 | 8.7 | 9.1 | 9.4 | 9.7 |
| | Mass Flow (Lbs/Hr) | 89.0 | 107.6 | 128.7 | 152.5 | 178.9 | 208.2 | 240.3 | 275.4 | 313.5 | 354.8 |
| | EER (Btu/(W Hr)) | 4.17 | 4.82 | 5.48 | 6.14 | 6.83 | 7.55 | 8.32 | 9.14 | 10.02 | 10.97 |

\* 24,000 Btuh @ 130° F Condenser & 45° F Evaporator

*FIG. 9*

Typical 15,000 Btuh* Compressor Performance Table

Refrigerant: R-22  
Motor: 2-Pole  
Subcooling: 15.0° F

Displacement: 1.717 in$^3$  
Voltage: 230-1-60  
Superheat: 20.0° F

| Condenser Temperature (°F) | | Evaporator Temperature (°F) | | | | | | | | |
|---|---|---|---|---|---|---|---|---|---|---|
| | | 5 | 10 | 15 | 20 | 25 | 30 | 35 | 40 | 45 |
| 80 | Capacity (Btu/Hr) | 8021 | *9510* | 11144 | 12932 | 14887 | 17020 | 19342 | 21865 | 24600 |
| | Power (watts) | 869 | 905 | 935 | 960 | 979 | 995 | 1006 | 1015 | 1020 |
| | Current (Amps) | 3.8 | 3.9 | 4.0 | 4.1 | 4.2 | 4.2 | 4.2 | 4.2 | 4.1 |
| | Mass Flow (Lbs/Hr) | 101.4 | 119.2 | 138.6 | 159.7 | 182.6 | 207.5 | 234.7 | 264.1 | 296.0 |
| | EER (Btu/(W Hr)) | 9.23 | 10.51 | 11.92 | 13.48 | 15.20 | 17.11 | 19.22 | 21.55 | 24.11 |
| 90 | Capacity (Btu/Hr) | 7207 | 8611 | 10144 | 11817 | 13642 | 15630 | 17793 | 20141 | 22687 |
| | Power (watts) | 901 | 946 | 984 | 1016 | 1042 | 1063 | 1079 | 1091 | 1100 |
| | Current (Amps) | 3.9 | 4.1 | 4.3 | 4.4 | 4.5 | 4.6 | 4.6 | 4.6 | 4.6 |
| | Mass Flow (Lbs/Hr) | 94.8 | 112.2 | 131.1 | 151.5 | 173.7 | 197.7 | 223.7 | 251.8 | 282.3 |
| | EER (Btu/(W Hr)) | 8.00 | 9.10 | 10.31 | 11.63 | 13.09 | 14.71 | 16.49 | 18.46 | 20.63 |
| 100 | Capacity (Btu/Hr) | 6359 | 7685 | 9125 | 10691 | 12393 | 14244 | 16255 | 18437 | 20801 |
| | Power (watts) | 922 | 978 | 1026 | 1067 | 1102 | 1130 | 1153 | 1171 | 1185 |
| | Current (Amps) | 4.0 | 4.2 | 4.5 | 4.6 | 4.8 | 4.9 | 5.0 | 5.1 | 5.1 |
| | Mass Flow (Lbs/Hr) | 87.1 | 104.3 | 122.8 | 142.7 | 164.1 | 187.2 | 212.3 | 239.3 | 268.5 |
| | EER (Btu/(W Hr)) | 6.90 | 7.86 | 8.89 | 10.02 | 11.25 | 12.61 | 14.10 | 15.74 | 17.56 |
| 110 | Capacity (Btu/Hr) | 5487 | 6743 | 8098 | 9564 | 11152 | 12873 | 14740 | 16762 | 18953 |
| | Power (watts) | 927 | 997 | 1057 | 1110 | 1155 | 1193 | 1225 | 1252 | 1273 |
| | Current (Amps) | 4.0 | 4.3 | 4.6 | 4.8 | 5.0 | 5.2 | 5.3 | 5.5 | 5.5 |
| | Mass Flow (Lbs/Hr) | 78.3 | 95.4 | 113.6 | 133.1 | 153.9 | 176.4 | 200.5 | 226.5 | 254.5 |
| | EER (Btu/(W Hr)) | 5.92 | 6.77 | 7.66 | 8.62 | 9.65 | 10.79 | 12.03 | 13.39 | 14.89 |
| 120 | Capacity (Btu/Hr) | 4603 | 5796 | 7074 | 8448 | 9929 | 11529 | 13259 | 15130 | 17155 |
| | Power (watts) | 915 | 1000 | 1075 | 1141 | 1199 | 1250 | 1293 | 1329 | 1360 |
| | Current (Amps) | 3.9 | 4.3 | 4.6 | 4.9 | 5.2 | 5.4 | 5.6 | 5.8 | 5.9 |
| | Mass Flow (Lbs/Hr) | 68.6 | 85.7 | 103.8 | 122.9 | 143.3 | 165.1 | 188.5 | 213.5 | 240.5 |
| | EER (Btu/(W Hr)) | 5.03 | 5.80 | 6.58 | 7.40 | 8.28 | 9.23 | 10.26 | 11.38 | 12.62 |
| 130 | Capacity (Btu/Hr) | 3719 | 4857 | 6066 | 7355 | 8737 | 10222 | 11823 | 13552 | 15418 |
| | Power (watts) | 880 | 983 | 1075 | 1158 | 1231 | 1295 | 1352 | 1401 | 1443 |
| | Current (Amps) | 3.8 | 4.2 | 4.6 | 5.0 | 5.3 | 5.6 | 5.8 | 6.1 | 6.3 |
| | Mass Flow (Lbs/Hr) | 58.0 | 75.2 | 93.2 | 112.1 | 132.2 | 153.5 | 176.2 | 200.5 | 226.5 |
| | EER (Btu/(W Hr)) | 4.22 | 4.94 | 5.64 | 6.35 | 7.10 | 7.89 | 8.75 | 9.67 | 10.69 |

\* 15,000 Btuh @ 130° F Condenser & 45° F Evaporator

*FIG. 9a*

Using data from the two typical compressor performance tables:

For a 10° Fahrenheit Evaporator temperature and a 115° liquid refrigerant temperature and using Fig. 9 table for a 24,000 Buth compressor, the rated capacity at these conditions (10° F Evaporator, 130° F condensor with 15° of subcooling is: 8641 Buth.

For a 10° Fahrenheit Evaporator, temperature and a 65° Fahrenheit Evaporator temperature and a 65° Fahrenheit liquid temperature (80° Fahrenheit condenser with 15° of subcooling) and using Fig. 9a table for a 15,000 Btuh compressor, the rated capacity at these conditions is: 9510 Btuh.

Therefore, theoretically, with 50° Fahrenheit of extra subcooling below normal air source condenser's subcooling, the compressor could be downsized by:

$$\frac{24 - 15}{24} \times 100 = 37.5\%$$

For example: An ice machine using a 3 hp compressor could be downsized to a 2 hp compressor if 50° Fahrenheit of extra, subcooling were accomplished, while still maintaining the same ice production rate.

FIG. 9b

UTILIZATION OF HARVEST AND/OR MELT WATER FROM AN ICE MACHINE FOR A REFRIGERANT SUBCOOL/PRECOOL SYSTEM AND METHOD THEREFOR

This application is a continuation of provisional application Ser. No. 60/087,372, filed May 28, 1998.

BACKGROUND OF THE INVENTION

1. Field of the Invention

The present invention relates to a subcool and/or precool system for the liquid refrigerant and/or hot gas discharge refrigerant of an ice machine that utilizes the harvest water and/or melt water from said ice machine for purposes of increasing the capacity and efficiency of said ice machine.

The present invention further relates to a system for capturing the harvest and/or melt water for utilization in the subcool/precool system.

The present invention also relates to a system for controlling the flow of said harvest and/or melt water through heat exchangers for purposes of subcooling and/or precooling the refrigerant.

The present invention additionally relates to a system for utilizing the harvest and/or melt water as a heat sink (no active pumping) for said subcooling and/or precooling of the refrigerant.

The present invention also further relates to a system for using excess refrigeration capability due to subcooling for purposes of precooling the incoming water supply.

Still further, the present invention relates to a system for using excess refrigeration capability due to subcooling for purposes of chilling the ice holding compartment to prevent excessive melt or degradation of ice that has already been produced.

Finally, the present invention relates to a method for downsizing the compressor of an ice machine to more closely match the refrigeration capability of the ice making plate with the additional capability due to the subcooling taken into account.

This invention more particularly pertains to an apparatus and method comprising a harvest and/or melt water-cooled subcooler positioned between a conventional air source or water source ice machine condenser and the evaporator. This invention also more particularly pertains to an apparatus and method comprising a harvest and/or melt water cooled precooler positioned between the compressor discharge of a conventional air source or water source ice machine and the condenser for said ice machine.

Next, this invention more particularly pertains to an apparatus and method whereby said harvest and/or melt water may be used first in said subcooler and then subsequently used in said precooler.

Additionally, this invention more particularly pertains to an apparatus and method comprising a reservoir for capturing and storing said harvest and/or melt water.

This invention also more particularly pertains to an apparatus and method comprising a pump and controls for purposes of directing and controlling the flow of said harvest and/or melt water through said subcooler and/or precooler heat exchangers.

This invention alternately more particularly pertains to an apparatus and method to direct said harvest and/or melt water into heat sink reservoirs for purposes of subcooling and/or precooling the refrigerant of an ice machine, without the use of directed flow heat exchangers.

This invention additionally more particularly pertains to an apparatus and method comprising an incoming water precooler positioned between the incoming water supply and the water control valve or after the water control valve but before the ice machine water reservoir and that is further positioned in the refrigerant circuit between the outlet of the ice making evaporator and the inlet to the compressor, whereby excess refrigeration effect due to subcooling may be used to precool the incoming water supply to said ice machine.

Also, this invention more particularly pertains to an apparatus and method comprising a secondary evaporator positioned between the outlet of the ice making evaporator and the inlet to the compressor, whereby excess refrigeration effect due to subcooling may be used to cool the ice holding compartment of the ice machine system.

Finally, this invention also more particularly pertains to an apparatus and method comprising the downsizing of the compressor of an ice machine to more closely match the ice production capability of the ice making evaporator to a compressor sized for the refrigeration capacity capability due to the subcooling accomplished by the harvest and/or melt water.

2. Description of the Background Art

Presently there exist many types of devices designed to operate in the thermal transfer cycle. The vapor-compression refrigeration cycle is the pattern cycle for the great majority of commercially available ice machine systems. This thermal transfer cycle is customarily accomplished by a compressor, condenser, throttling device and evaporator connected in serial fluid communication with one another. The system is charged with refrigerant, which circulates through each of the components. More particularly, the refrigerant of the system circulates through each of the components to remove heat from the evaporator and transfer heat to the condenser. The compressor compresses the refrigerant from a low-pressure superheated vapor state to a high-pressure superheated vapor state thereby increasing the temperature, enthalpy and pressure of the refrigerant. A superheated vapor is a vapor that has been heated above its boiling point temperature. It leaves the compressor and enters the condenser as a vapor at some elevated pressure where the refrigerant is condensed as a result of the heat transfer to cooling water and/or to ambient air. The refrigerant then flows through the condenser condensing the refrigerant at a substantially constant pressure to a saturated-liquid state. The refrigerant then leaves the condenser as a high pressure liquid. The pressure of the liquid is decreased as it flows through the expansion valve causing the refrigerant to change to a mixed liquid-vapor state. The remaining liquid, now at low pressure, is vaporized in the evaporator as a result of heat transfer from the refrigerated space. This vapor then enters the compressor to complete the cycle. The ideal cycle and hardware schematic for vapor compression refrigeration is shown in FIG. 1 as cycle 1-2-3-4-1. More particularly, the process representation in FIG. 1 is represented by a pressure-enthalpy diagram, which illustrates the particular thermodynamic characteristics of a typical refrigerant. The P-h plane is particularly useful in showing the amounts of energy transfer as heat. Referring to FIG. 1, saturated vapor at low pressure enters the compressor and undergoes a reversible adiabatic compression, 1–2. Adiabatic refers to any change in which there is no gain or loss of heat. Heat is then rejected at constant pressure in process 2–3. An adiabatic pressure change occurs through the expansion device in process 3–4, and the working fluid is then evaporated at constant pressure, process 4–1, to complete the cycle. However, the actual refrigeration cycle may deviate from the ideal cycle primarily because of pressure drops associated with fluid flow and heat transfer to or from the surroundings. It is readily apparent that the temperature of the liquid refrigerant plays an important role in the potential for removing heat in the evaporator phase of the thermal cycle. The colder the liquid refrigerant entering the evaporator, the greater the possible change in enthalpy or heat energy absorbed per unit mass of liquid available for vaporization and the colder the liquid refrigerant entering the expansion device leading to the evaporator, the lower the flash gas loss, which means a higher portion or percentage of mass is available for vaporization through the evaporator. Finally, it is readily apparent that rapid precooling of the hot gas discharge from a compressor lowers power consumption, reduces heat discharge by an air cooled condenser, improves compressor efficiency and improves the primary condenser's performance. Many such devices and methods currently exist that are designed to accomplish this subcooling and precooling.

However, these known methods and devices have drawbacks. The drawbacks include high cost of accomplishing the subcooling and/or precooling, and/or the ineffectiveness or degrading effectiveness of the subcooling and/or precooling, method and/or device.

In response to the realized inadequacies of earlier methods and devices, it became clear that there is a need for a liquid refrigerant subcooler for an ice machine that has a low initial cost as well as having a method for utilizing the previously unused, very cold heat sink available in the form of the harvest and/or melt water being discharged and subsequently thrown away from an ice machine.

It is also readily apparent that rapid precooling of the hot gas discharge from a compressor reduces head pressure, decreases power consumption, reduces heat being discharged into the ambient air surrounding an ice machine and improves the efficiency of the primary condenser of an ice machine system.

The use of the harvest and/or melt water coming off of the ice machine or even after use in the subcooler will provide this precooling in a very cost effective manner.

Therefore the principal objective of this invention is to provide an improvement which overcomes the aforementioned inadequacies of the prior art devices and provides an improvement which is a significant contribution to the advancement of the subcooler and precooler art for ice machines.

Another objective of the present invention is to provide a more constant and colder subcooling over a wide range of air source conditions.

Still another objective of the present invention is to provide harvest and/or melt water cooling to the liquid refrigerant of an ice machine system.

Yet another objective of the present invention is to provide increased refrigeration capacity and ice making capacity by means of the subcooling of the liquid refrigerant.

An additional objective of the present invention is to provide a means of utilizing excess refrigeration capacity due to subcooling by adding an evaporator surface that will precool the incoming water supply.

Still a further objective of the present invention is to provide a means of utilizing excess refrigeration capacity due to subcooling by adding an evaporator surface that will cool the ice storage chamber/compartment.

Yet a further objective of the present invention is to provide a means of downsizing the ice machine compressor to compensate for excess refrigeration capacity due to subcooling of the liquid refrigerant.

Still yet another objective of the present invention is to provide rapid precooling of the hot gas discharge from a compressor utilizing the harvest and/or melt water from and ice machine system, or after first using said harvest and/or melt water to subcool the liquid refrigerant.

And yet another objective of the present invention is to provide lower power consumption, increased pumping efficiency of the compressor, decreased heat rejection to the ambient air surrounding an ice machine, as well as to improve the primary condenser's performance.

Even yet another objective of the present invention is to provide a means for capturing, storing and preventing heat gains to the harvest and/or melt water discharge from an ice machine system.

And yet another objective of the present invention is to provide a means for pumping and controlling the flow of the stored harvest and/or melt water through the subcooler and/or precooler heat exchangers.

And yet another objective of the present invention is to provide an alternative means of utilizing the harvest and/or melt water to subcool and/or precool the refrigerant of an ice machine, by providing thermal heat sink storage tanks where subcooling and/or precooling with the total harvest and/or melt water available from each cycle may be accomplished in lieu of pumping said harvest and/or melt water through subcooler and/or precooler heat exchangers.

The foregoing has outlined some of the pertinent objects of the invention. These objects should be construed to be merely illustrations of some of the more prominent features and applications of the intended invention. Many other beneficial results can be obtained by applying the disclosed invention in a different manner or by modifying the invention within the scope of the disclosure.

Accordingly, other objects and a more comprehensive understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

The present invention is defined by the appended claims with the specific embodiment shown in the attached drawings. The present invention is directed to a first apparatus that satisfies the need for increased refrigeration effect by means of increased liquid refrigerant subcooling accomplished by utilizing the cold heat sink temperature available from the harvest and/or melt water discharge from an ice machine. For the purpose of summarizing this first apparatus and means of the invention, the liquid refrigerant line coming off of an air or water source condenser of an ice machine is serially connected to a tube in tube, tube on tube, flat plate or shell and tube type subcool heat exchanger before then being connected to the line leading to the expansion device of an ice making system. The cold harvest and/or melt water discharge water from an ice machine being directed through said tube in tube, tube on tube, flat plate or shell and tube type subcool heat exchanger, from a retention area. The harvest and/or melt water flow being controlled for maximum effect and minimal use by means of control devices and a pump.

Simply, this first apparatus allows subcooling of the liquid refrigerant by means of the cold harvest and/or melt water discharge water from an ice machine system needing the additional refrigeration effect caused by the refrigerant subcooling.

Moreover, this present invention may be configured by means of a second apparatus that satisfies the need for lower power consumption, increased pumping efficiency of the compressor, decreased heat rejection to the ambient air surrounding an ice machine, as well as for improving the primary condenser's performance by means of increased hot gas refrigerant precooling accomplished by utilizing the cold heat sink temperature available from the harvest and/or melt water discharge water from an ice machine or by utilizing said harvest and/or melt water after first using it in the subcooler of the first apparatus. For the purposes of summarizing this second apparatus and means of the invention, the hot gas discharge line coming off of the compressor of an ice machine system is serially connected to a tube in tube, tube on tube, flat plate or shell and tube type precool heat exchanger before then being connected to the hot gas line leading to the condenser. The cold harvest and/or melt water discharge water from an ice machine being directed (or after first being directed through the subcooler of the first apparatus) through said tube in tube, tube on tube, flat plate or shell and tube type precool heat exchanger from a retention area (or from said subcooling apparatus). The harvest and/or melt water flow being controlled for maximum effect and minimal use by means of control devices and a pump.

Simply, this second apparatus allows precooling of the hot gas refrigerant by means of the cold harvest and/or melt water discharge water from an ice machine or by means of the discharge of the water from the subcooler of the first apparatus where the harvest and/or melt water is first used to subcool the liquid refrigerant and then used subsequently to precool the hot gas refrigerant.

Additionally, this present invention may be configured by means of an alternate first apparatus and/or second apparatus, configured in such a way that storage of the harvest and/or melt water is provided in such a manner that the storage container or containers provide a direct heat sink for the liquid refrigerant line and/or the hot gas refrigerant discharge line, without the use of a pump, heat exchangers or controls for water flow.

Simply, this alternate first and/or second apparatus allows subcooling of the liquid refrigerant by means of a passive heat sink use (with no active pumping) of the harvest and/or melt water discharge water from an ice machine system and/or allows precooling of the hot gas refrigerant discharge by means of a first and/or secondary passive heat sink use (with no active pumping) of the harvest and/or melt water discharge water from an ice machine system.

Further, this present invention may be configured by means of a third apparatus in such a way that excess refrigeration capacity, due to subcooling of the liquid refrigerant, can be utilized by adding an incoming water precooler that is in addition to the existing ice making evaporator. The precooler being serially connected in the refrigeration circuit between the outlet of the ice making evaporator and the suction gas inlet to the compressor, and further being serially connected in the water circuit between the water inlet to the ice machine system and the water inlet to the ice machine reservoir, with means included to bypass the inlet water precooler with the refrigerant during the harvest cycle of the ice machine.

Simply, this third apparatus allows precooling of the incoming water supply before the reservoir, thereby providing for a shorter ice making production time.

Also, this present invention may be configured by means of a fourth apparatus in such a way that excess refrigeration capacity, due to subcooling of the liquid refrigerant, can be utilized by adding a storage bin chiller that is in addition to the existing ice making evaporator. The chiller being serially connected in the refrigeration circuit between the outlet of the ice making evaporator (or before or after the water precooler) and the suction gas inlet to the compressor, with means included to bypass the storage bin chiller with the refrigerant during the harvest cycle of the ice machine.

Simply, a fourth apparatus allows cooling of the ice storage bin thereby providing for decreased ice melting and degradation.

Finally, this present invention may be configured by means of including downsizing of the existing compressor of an ice machine system to accommodate for the increased refrigeration effect due to subcooling which may surpass the capacity of the existing ice making evaporator plate.

Simply, this means, allows for reduced compressor size and thereby power consumption while maintaining the ice production capacity of the existing ice making evaporator plate.

The foregoing has outlined rather broadly, the more pertinent and important features of the present invention. The detailed description of the invention that follows is offered so that the present contribution to the art can be more fully appreciated. Additional features of the invention will be described hereinafter. These form the subject of the claims of the invention. It should be appreciated by those skilled in the art that the conception and the disclosed specific embodiment may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more succinct understanding of the nature and objects of the present invention, reference should be directed to the following detailed description taken in connection with the accompanying drawings in which:

FIG. 3a is a perspective view showing some of the possible relationships of the hot gas discharge refrigerant and harvest and/or melt water flow through various types of refrigerant to fluid heat exchangers.

FIG. 9 is a typical compressor performance table showing the different capacities possible at different liquid temperatures.

FIG. 9a is a typical compressor performance table for a smaller compressor showing the different capacities at different liquid temperatures.

FIG. 9b shows the calculations utilizing data from FIGS. 9 and 9a that would allow downsizing of the compressor for an ice machine where an additional 50 degrees of subcooling is available.

DETAILED DESCRIPTION OF THE PREFERRED EMBODIMENT

With reference to the drawings, and in particular to FIGS. 2, 2a, 2b, 3, 3a, 3b, 4, 4a, 4b, 5, and 6 thereof, new and improved subcooling and/or precooling devices for improved refrigeration and ice making and/or capacity and/or increased efficiency, lower power consumption, decreased heat rejection to the ambient air surrounding an ice machine and improved primary condenser performance, embodying the principles and concepts of the present invention and generally designated by the reference number (10) for the subcooler only, and generally designated by the reference number (11) for the precooler only will be described.

Figure 1:
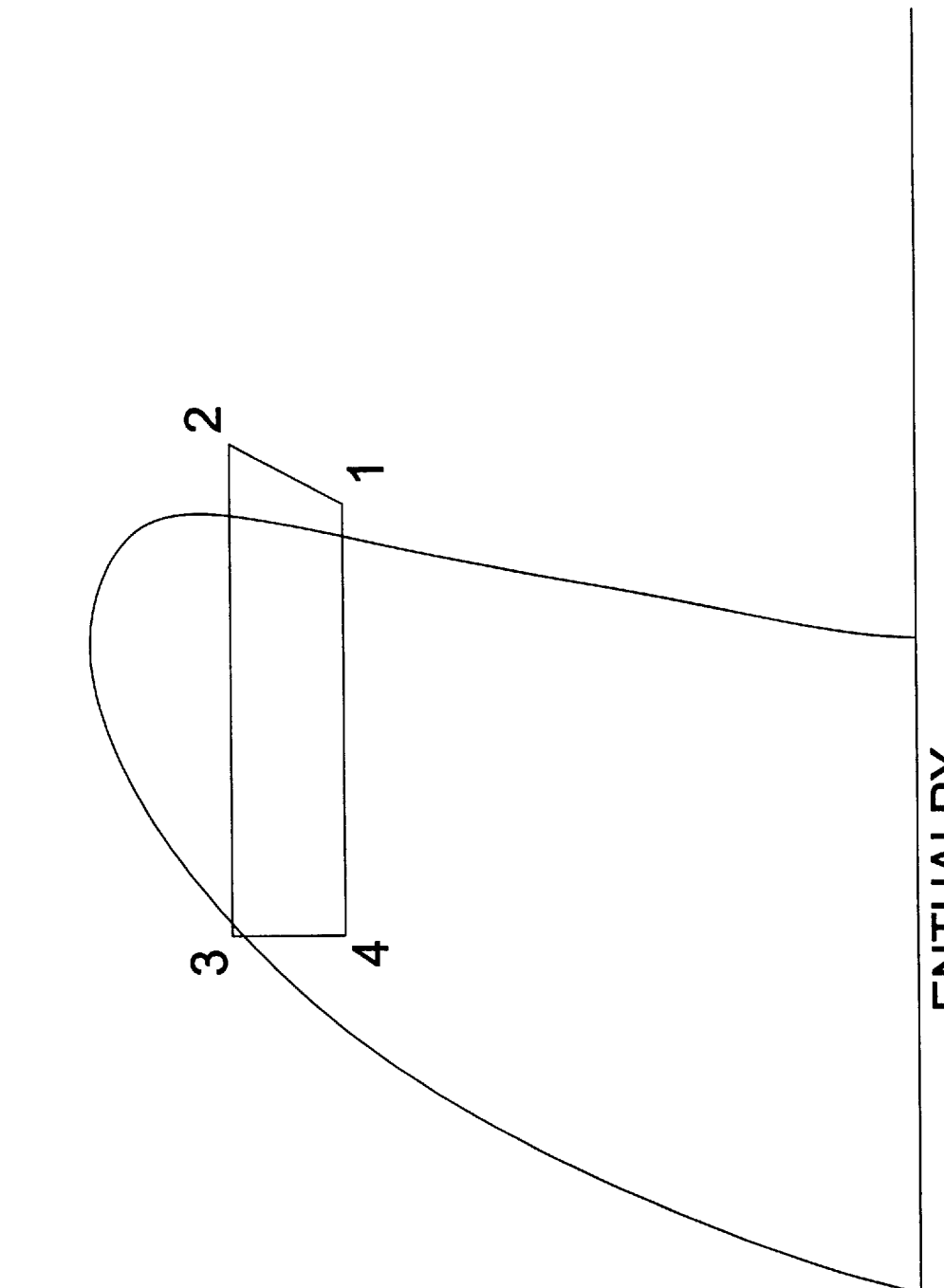
FIG. 1 is a representation of the refrigeration process on a pressure enthalpy diagram.
Figure 2:
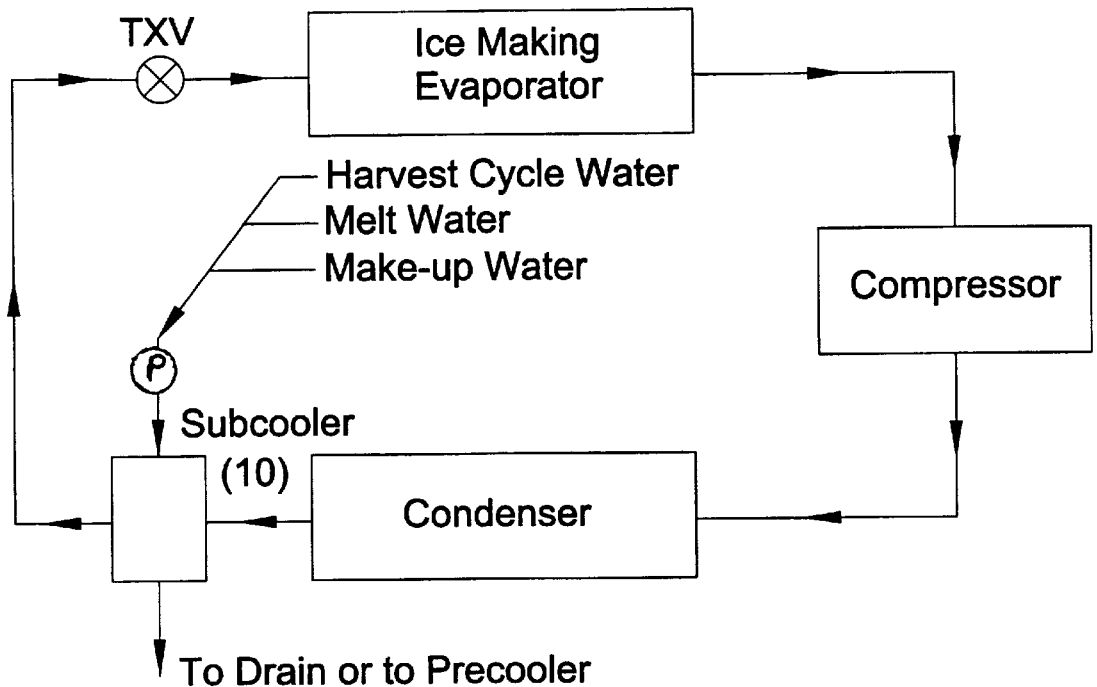
FIG. 2 is a hardware schematic of the vapor compression cycle for an ice machine system showing the location of the harvest and/or melt water cooled subcooler.
Figure 2A:
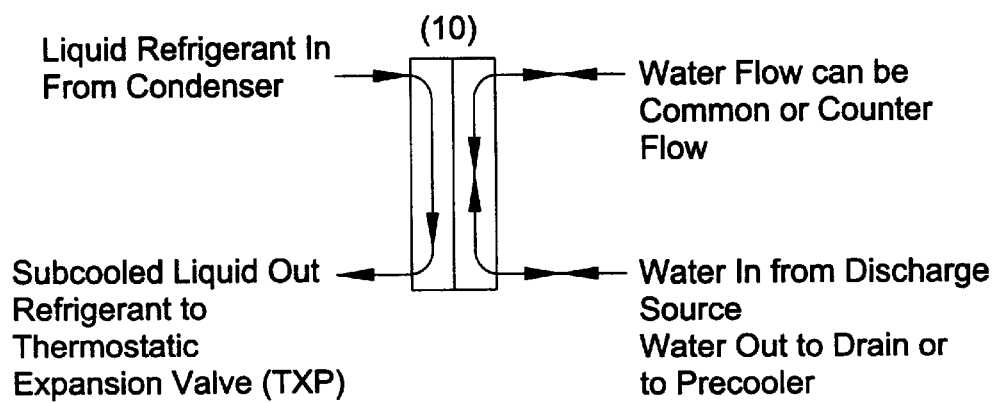
FIG. 2a is a perspective view showing some of the possible relationships of liquid refrigerant and harvest and/or melt water flow through various types of refrigerant to fluid heat exchangers.
Figure 2B:
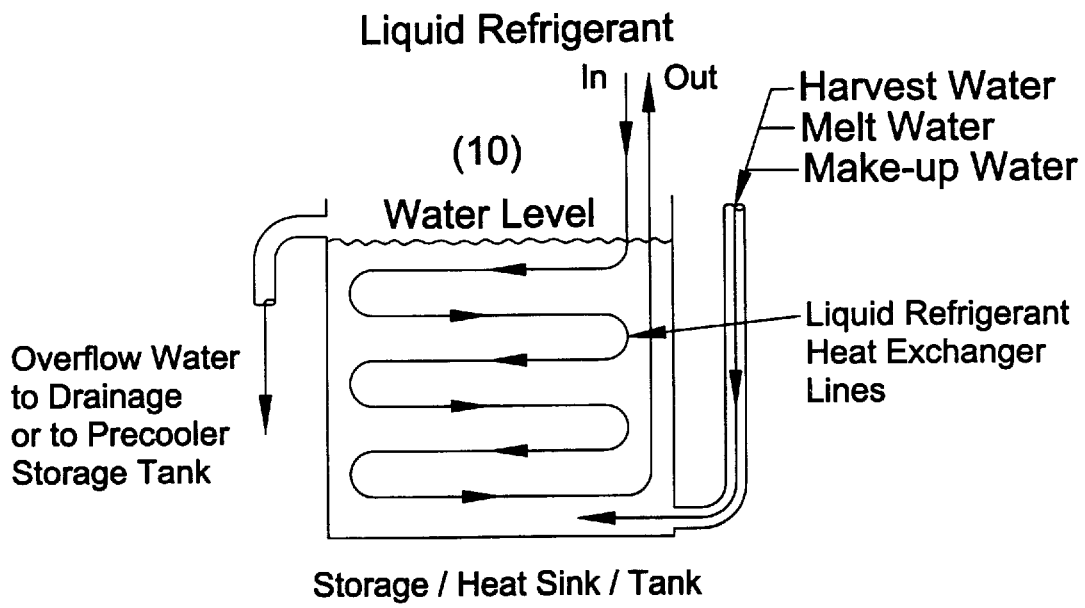
FIG. 2b is a perspective view showing the relationship between the liquid refrigerant and the harvest and/or melt water as utilized in a heat sink system.

First, for the subcooler system only (10), of the present invention, as illustrated in FIGS. 2, 2a and 2b, a subcooler for the liquid refrigerant relies on one heat sink source; a direct use of the harvest and/or melt water discharge from the ice machine that will utilize said subcooled liquid refrigerant. The harvest and/or melt water source subcooler is to be connected in serial communication in the refrigeration cycle as shown in FIG. 2. This embodiment of the present invention may have various configurations, comprising a variety of heat exchanger types (FIG. 2a or FIG. 2b) relying on the harvest and/or melt water discharge to provide liquid subcooling with said water being pumped through the heat exchangers of FIG. 2a, or used passively as shown in FIG. 2b. In FIG. 2a the water flow through the heat exchangers could be either counter flow (most efficient) or common flow to the direction of the flow of the refrigerant through the subcool heat exchanger.

Figure 3B:
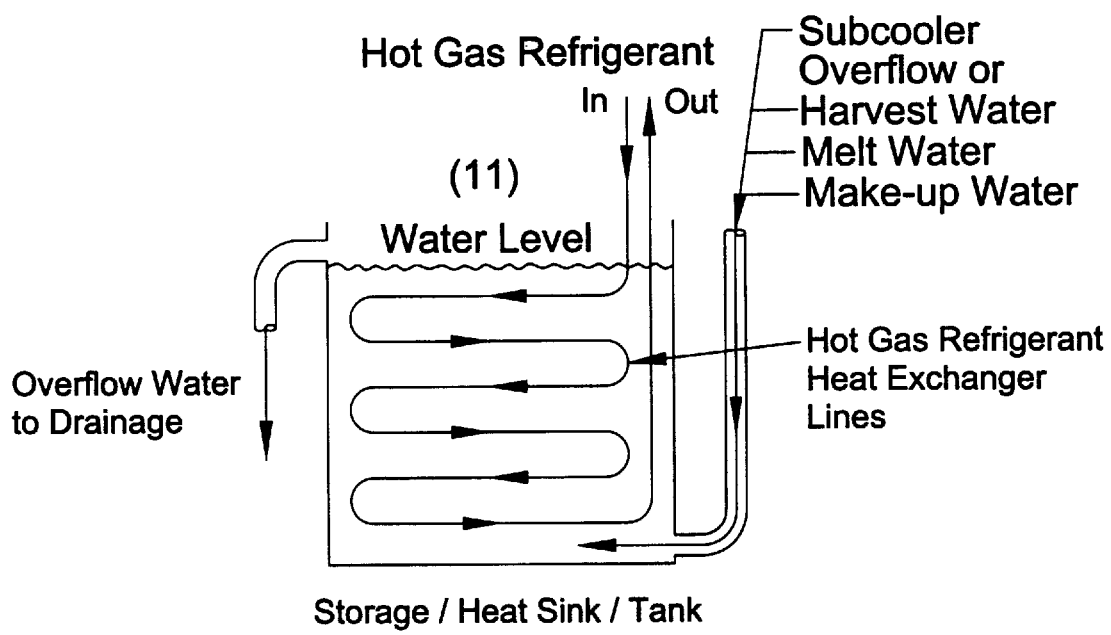
FIG. 3b is a perspective view showing the relationship between the liquid refrigerant and the harvest and/or melt water as utilized in a heat sink system.
Figure 3:
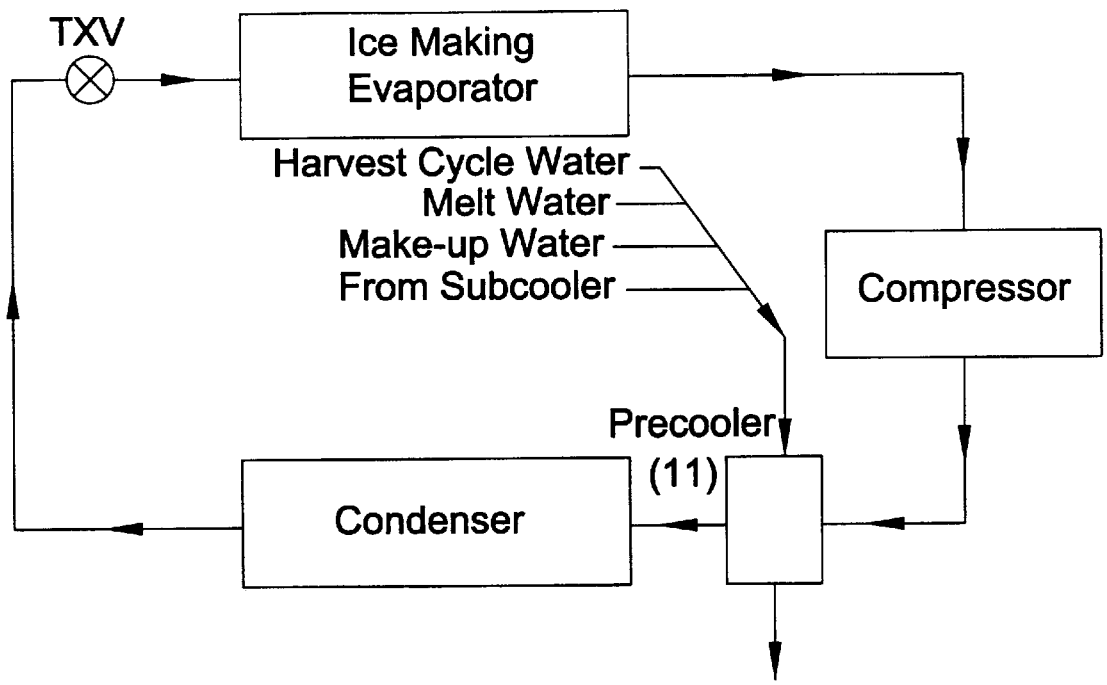
FIG. 3a hardware schematic of the vapor compression cycle for an ice machine showing the location of the harvest and/or melt water cooled precooler.
Figure 3A:
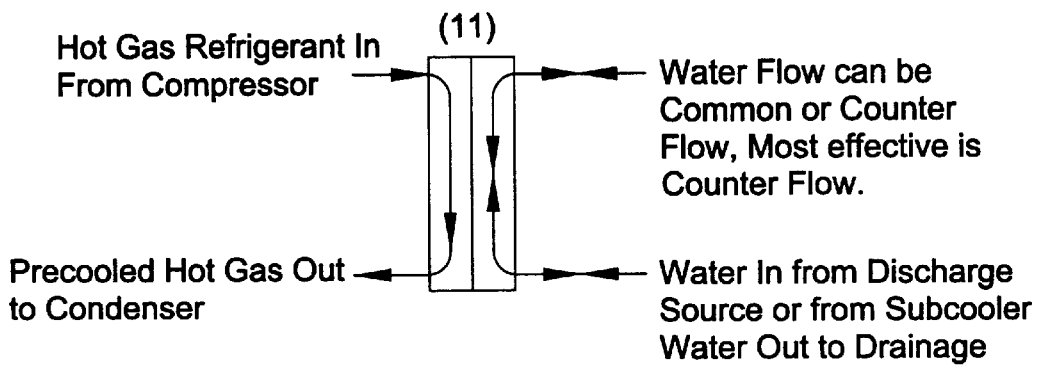

For the precooler system only (11) of the present invention, as illustrated in FIGS. 3, 3a and 3b, a precooler for the hot gas refrigerant relies on one heat sink source; a direct use of the harvest and/or melt water discharge from the ice machine that will utilize the benefits of the precooler, or the secondary use of the harvest and/or melt water discharge after first being used in the subcooler. The harvest and/or melt water source precooler to be connected in serial communication in the refrigeration cycle as shown in FIG. 3. This embodiment of the present invention may have various configurations, comprising a variety of heat exchanger types (FIG. 3a or FIG. 3b) relying on the harvest and/or melt water discharge to provide hot gas precooling with said water being pumped through the heat exchangers of FIG. 3a, or used passively as shown in FIG. 3b. In FIG. 3a the water flow through the heat exchangers could be either counter flow (most efficient) or common flow to the direction of the flow of the refrigerant through the precool heat exchanger.

Figure 4:
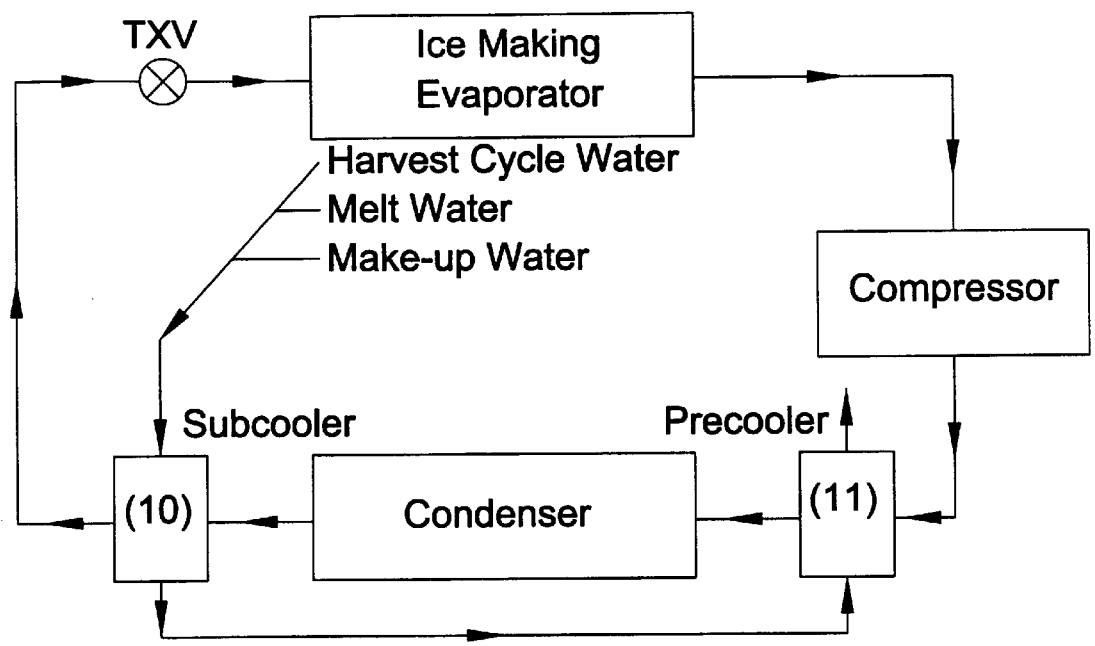
FIG. 4 is a hardware schematic of the vapor compression cycle for an ice machine showing the location of the combined harvest and/or melt water cooled subcooler plus secondary use combined harvest and/or melt water cooled precooler.
Figure 4A:
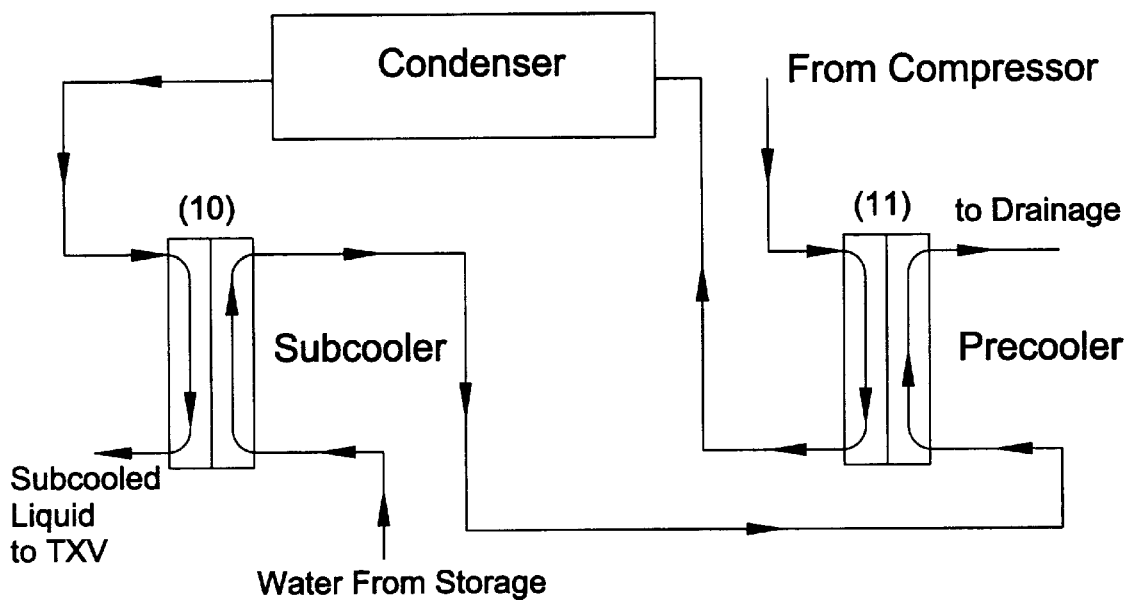
FIG. 4a is a perspective view showing the relationship between the liquid refrigerant subcool heat exchanger and the hot gas refrigerant precool heat exchanger and the possible flow direction of the harvest and/or melt water flow through said subcooler and precooler.
Figure 4B:
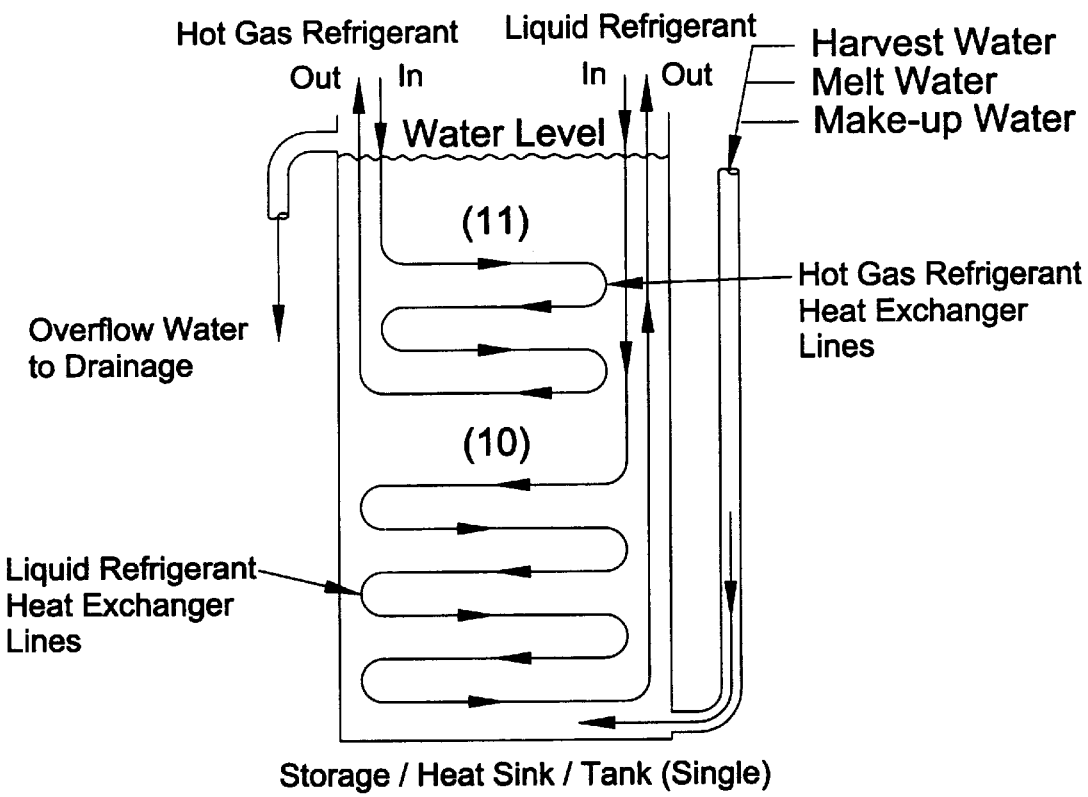
FIG. 4b is a perspective view showing some of the possible relationships between the liquid refrigerant and hot gas refrigerant and the harvest and/or melt water as utilized in a heat sink system.
Figure 4B:
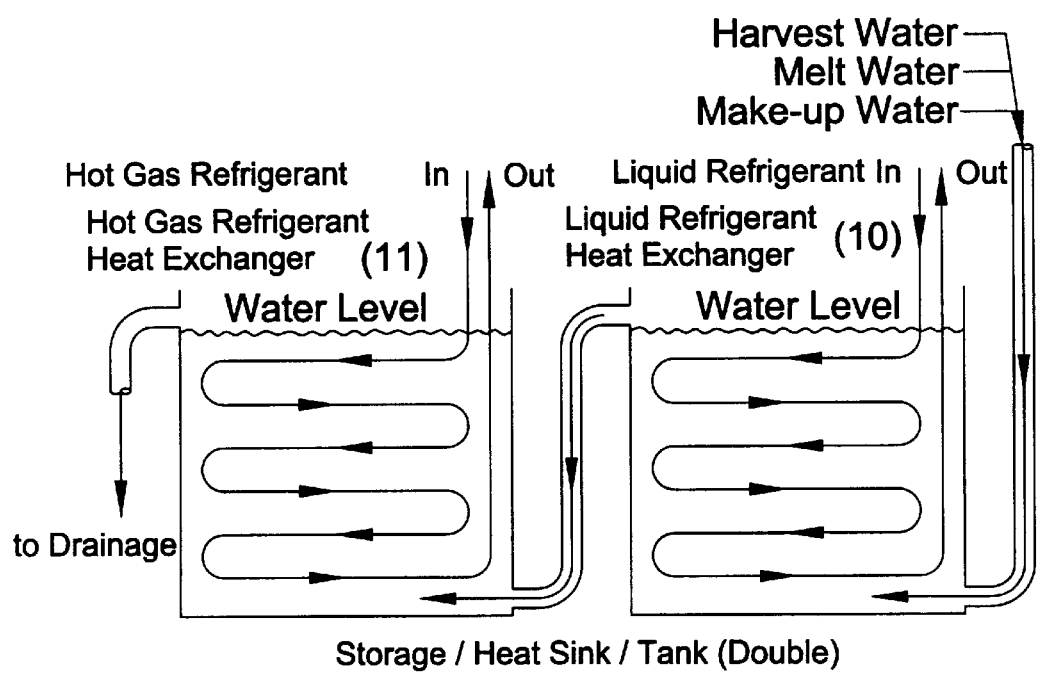

For the subcooler (10) plus precooler (11) combination of the present invention, as illustrated in FIGS. 4, 4a and 4b, a subcooler (10) for the liquid refrigerant and a precooler (11) for the hot gas refrigerant relies on one heat sink source that will be used twice; a direct use of the harvest and/or melt water discharge from the ice machine that will first flow through a subcooler and then flow through a precooler where said ice machine will utilize the benefits of said subcooler and precooler. The harvest and/or melt water source subcooler and precooler to be connected in serial communication in the refrigeration cycle as shown in FIG. 4. This embodiment of the present invention may have various configurations, comprising a variety of heat exchanger types (FIG. 4a or FIG. 4b) relying on the harvest and/or melt water discharge to provide subcooling of the liquid refrigerant and said harvest and/or melt water being used a second time to provide precooling of the hot gas refrigerant with said water being pumped through the heat exchangers of FIG. 4a, or used passively as shown in FIG. 4b. In FIG. 4a the water flow through the heat exchangers could be either counter flow (most efficient) or common flow to the direction of the flow of the refrigerant through the subcool and precool heat exchangers.

Figure 5:
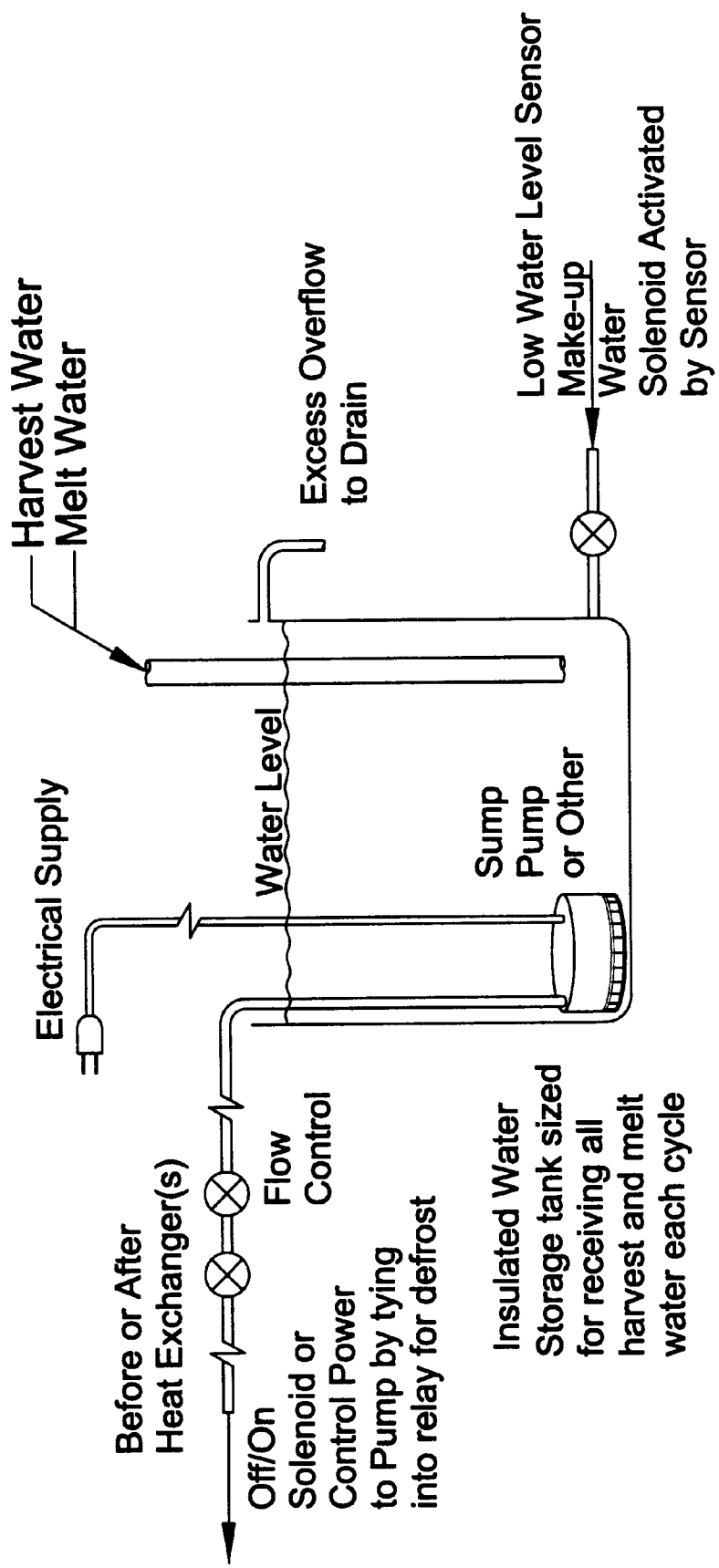
FIG. 5 is a hardware schematic showing some of the possible pump and control mechanisms for controlling the flow of harvest and/or melt water through the subcooler and/or precooler.

FIG. 5 is illustrative of some of the possible pump and control mechanisms for controlling rate of flow and flow of harvest and/or melt water through the subcooler and/or precooler.

Figure 6:
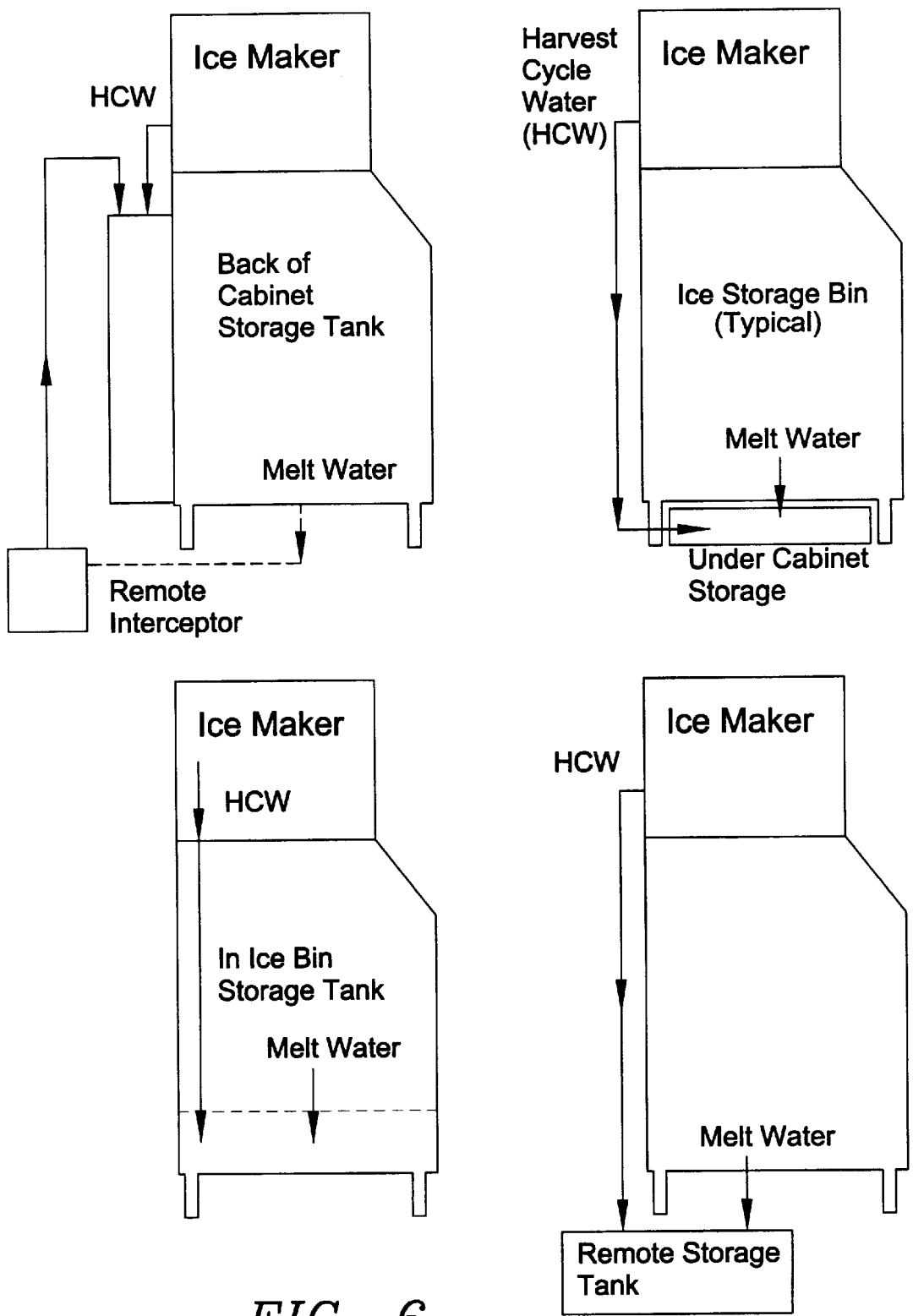
FIG. 6 is a hardware schematic showing some of the possible collection and storage methods for collecting and storing the harvest and/or melt water.

FIG. 6 is illustrative of some of the possible collection and storage systems and methods for collecting and storing the harvest and/or melt water.

Figure 7:
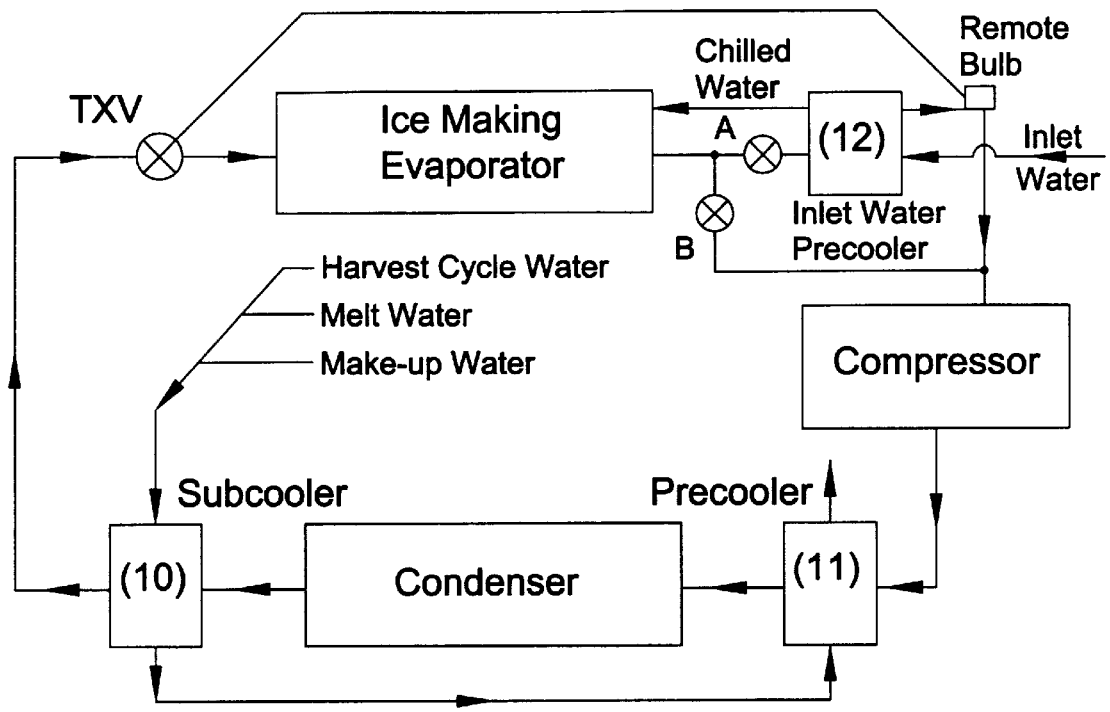
FIG. 7 is a hardware schematic showing the location of the incoming water precooler in the vapor compression cycle and water supply system of an ice machine.
Figure 7A:
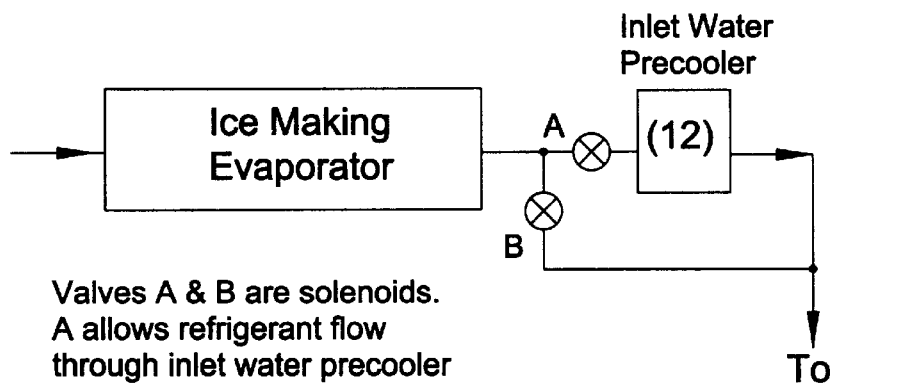
FIG. 7a is a perspective view showing some of the possible methods and controls for use with the incoming water precooler.

For the incoming water precooler (12) of the present invention, as illustrated in FIGS. 7 and 7a, the incoming water precooler for an ice machine relies on the excess refrigeration capacity provided to the ice machine by the subcooled liquid refrigerant to precool the incoming water supply to the ice machine system. The incoming water precooler is to be connected in serial communication in the refrigeration cycle and in the water supply to the water reservoir as shown in FIG. 7. This embodiment of the present invention may have various configurations, comprising a variety of heat exchanger types, reservoirs, controls and methods as shown in FIG. 7a.

Figure 8:
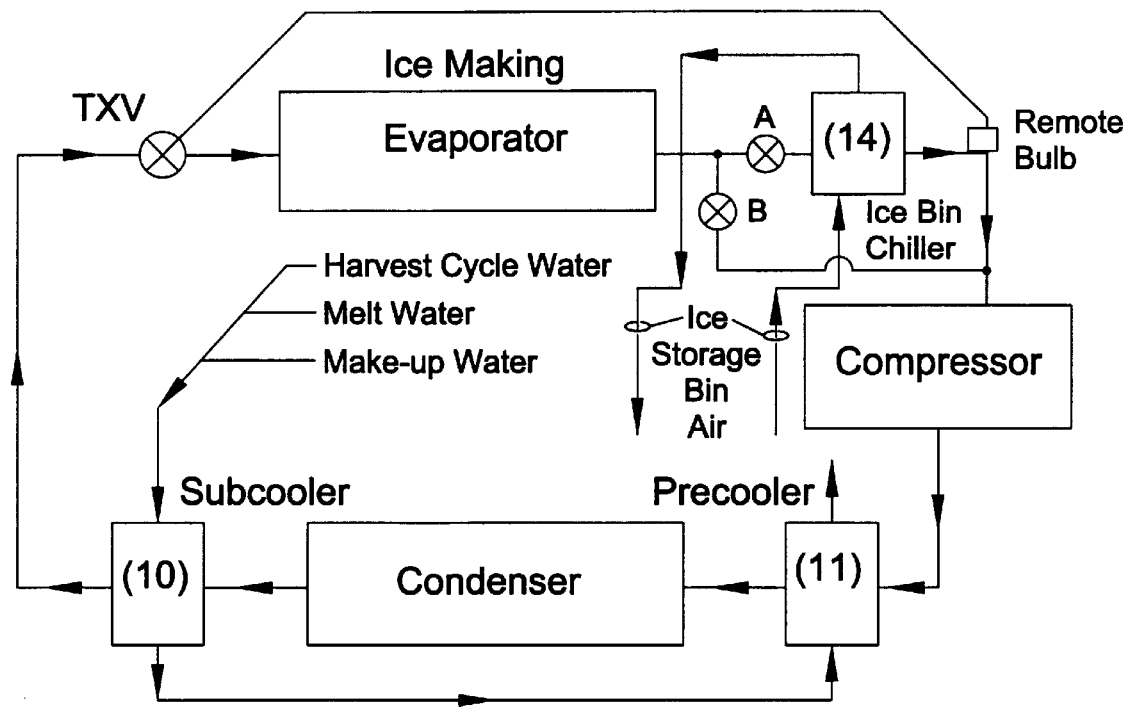
FIG. 8 is a hardware schematic showing the location of the ice storage bin chiller in the vapor compression cycle of an ice machine.
Figure 8A:
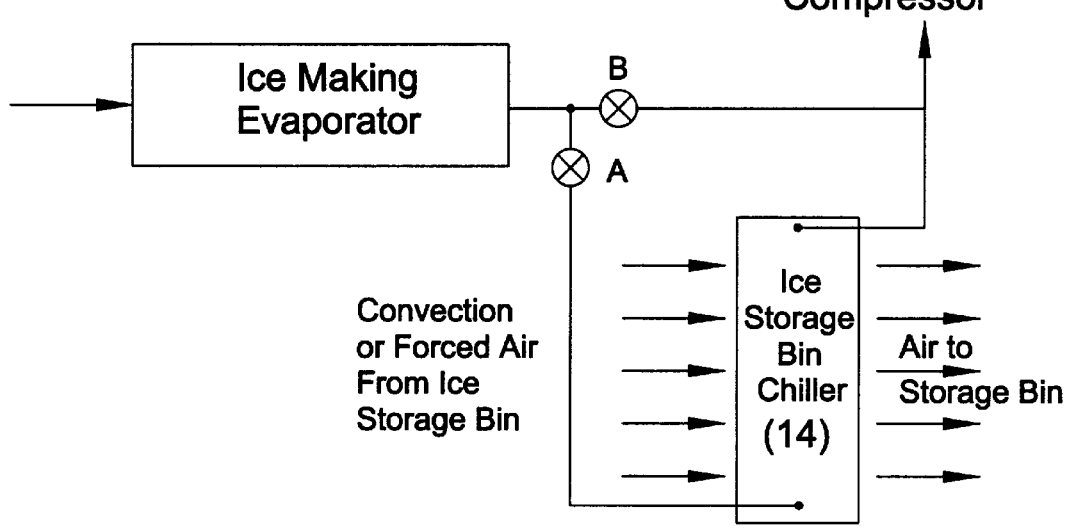
FIG. 8a is a perspective view showing some of the possible methods and controls for use with the ice storage bin chiller.

For the storage bin chiller (14) of the present invention, as illustrated in FIGS. 8 and 8a, the storage bin chiller for an ice machine system relies on the excess refrigeration capacity provided to the ice machine by the subcooled liquid refrigerant to chill the ice storage area of an ice machine system. The storage bin chiller is to be connected in serial communication in the refrigeration cycle as shown in FIG. 8. This embodiment of the present invention may have various configurations, comprising a variety of locations, heat exchanger types, controls and methods as shown in FIG. 8a.

FIGS. 9, 9a and 9b are illustrative of the various capacities a compressor is capable of at different operating conditions which illustrate the possibility of downsizing the compressor to match the existing ice making evaporator's capacity to a compressor sized for the capacity that is provided by the subcooling possible with this system. This would be in lieu of utilization of excess capacity by either the incoming water precooler or ice storage bin chiller.

The increase in efficiency due to subcooling is well known and is due to the increase in capacity due to subcooling of the liquid refrigerant. What is unique in this invention is the innovative use of the cold harvest and/or melt water that is typically discharged from an ice machine. The increased efficiency of the refrigeration cycle due to precooling is due to lower head pressures, higher compressor efficiency and more efficient use of the primary condenser. Also significant reduction of the rejection of the heat to the ambient air surrounding an air-cooled ice machine condenser is another byproduct. This reduces the air conditioning load due to the ice machine significantly. The unique and innovative use of the harvest and/or melt water discharge from an ice machine directly or indirectly after use in the subcooler is extremely cost effective.

The present disclosure includes that contained in the appended claims, as well as that of the foregoing description. Although this invention has been described in its preferred form with a certain degree of particularity, it could be understood that the present disclosure of the preferred form has been made only by way of example and that numerous changes in the details of construction and the combination and arrangement of parts may be resorted to without departing from the spirit and scope of the invention.

Now that the invention has been described, What is claimed is:

1. A heat exchange refrigerant subcool system that utilizes stored discharge water from an ice machine that is then pumped through a heat exchanger for subcooling a refrigerant that has already passed through the condenser of said ice machine, comprising in combination:

a subcooler connected in fluid communication with the output of the condenser, enabling the refrigerant to flow in a first direction through said subcooler after first flowing through the condenser; and said subcooler connected in fluid communication with the output of a pump that pumps stored ice machine discharge water to directly flow through said subcooler from a bottom portion to a top portion in a second direction opposite to said first direction and then to discharge;

whereby said subcooler utilizes the pumped and flowing cold discharge water from an ice machine for providing maximum available subcooling to the liquid refrigerant of said ice machine.

* * * * *